(12) United States Patent
Passmore et al.

(10) Patent No.: US 6,416,780 B1
(45) Date of Patent: Jul. 9, 2002

(54) INTRAVAGINAL DRUG DELIVERY DEVICES FOR THE ADMINISTRATION OF TESTOSTERONE AND TESTOSTERONE PRECURSORS

(75) Inventors: Clare Passmore; Claire Gilligan, both of Belfast (GB)

(73) Assignee: Galen (Chemicals) Limited, Tallaght (IE)

(*) Notice: Subject to any disclaimer, the term of this patent is extended or adjusted under 35 U.S.C. 154(b) by 0 days.

(21) Appl. No.: 09/423,324
(22) PCT Filed: May 7, 1998
(86) PCT No.: PCT/IE98/00033
§ 371 (c)(1),
(2), (4) Date: May 1, 2000
(87) PCT Pub. No.: WO98/50016
PCT Pub. Date: Nov. 12, 1998

(30) Foreign Application Priority Data
May 7, 1997 (GB) ............................................... S970333
(51) Int. Cl.[7] .................................................. A61F 9/02
(52) U.S. Cl. ...................... 424/436; 424/426; 424/430; 424/432; 424/444
(58) Field of Search ................................ 424/430, 432, 424/444, 424, 436

(56) References Cited

U.S. PATENT DOCUMENTS

| | | | |
|---|---|---|---|
| 3,920,805 A | | 11/1975 | Roseman ...................... 424/15 |
| 5,340,585 A | * | 8/1994 | Pike et al. .................. 424/426 |
| 5,855,906 A | | 1/1999 | McClay ....................... 434/433 |

* cited by examiner

Primary Examiner—Deborah D. Carr
(74) Attorney, Agent, or Firm—Jay H. Maioli

(57) ABSTRACT

This invention relates to an intravaginal shell or core drug delivery device suitable for administration to female humans or animals comprises testosterone or a testosterone precursor in a polymer matrix, surrounded by a sheath, and is capable of releasing the testosterone or testosterone precursor in a substantially zero-order pattern on a daily basis for at least three weeks. The device is intended to restore circulating testosterone levels to the normal physiol, range or to induce supratherapeutic testosterone levels.

9 Claims, 2 Drawing Sheets

Figure 1:
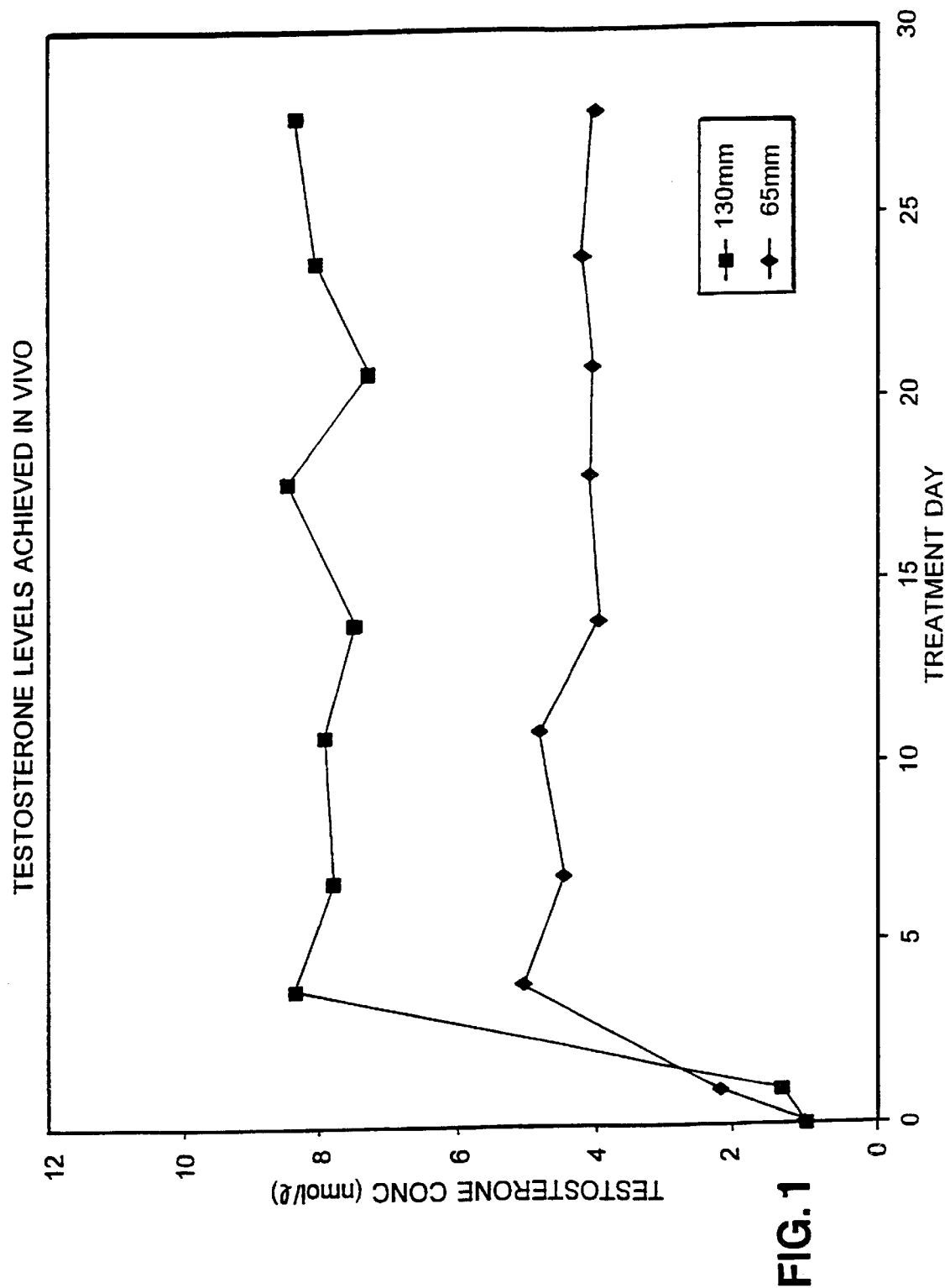

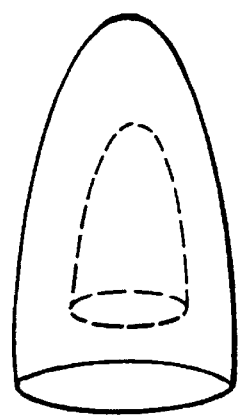
FIG. 2
FIG. 3
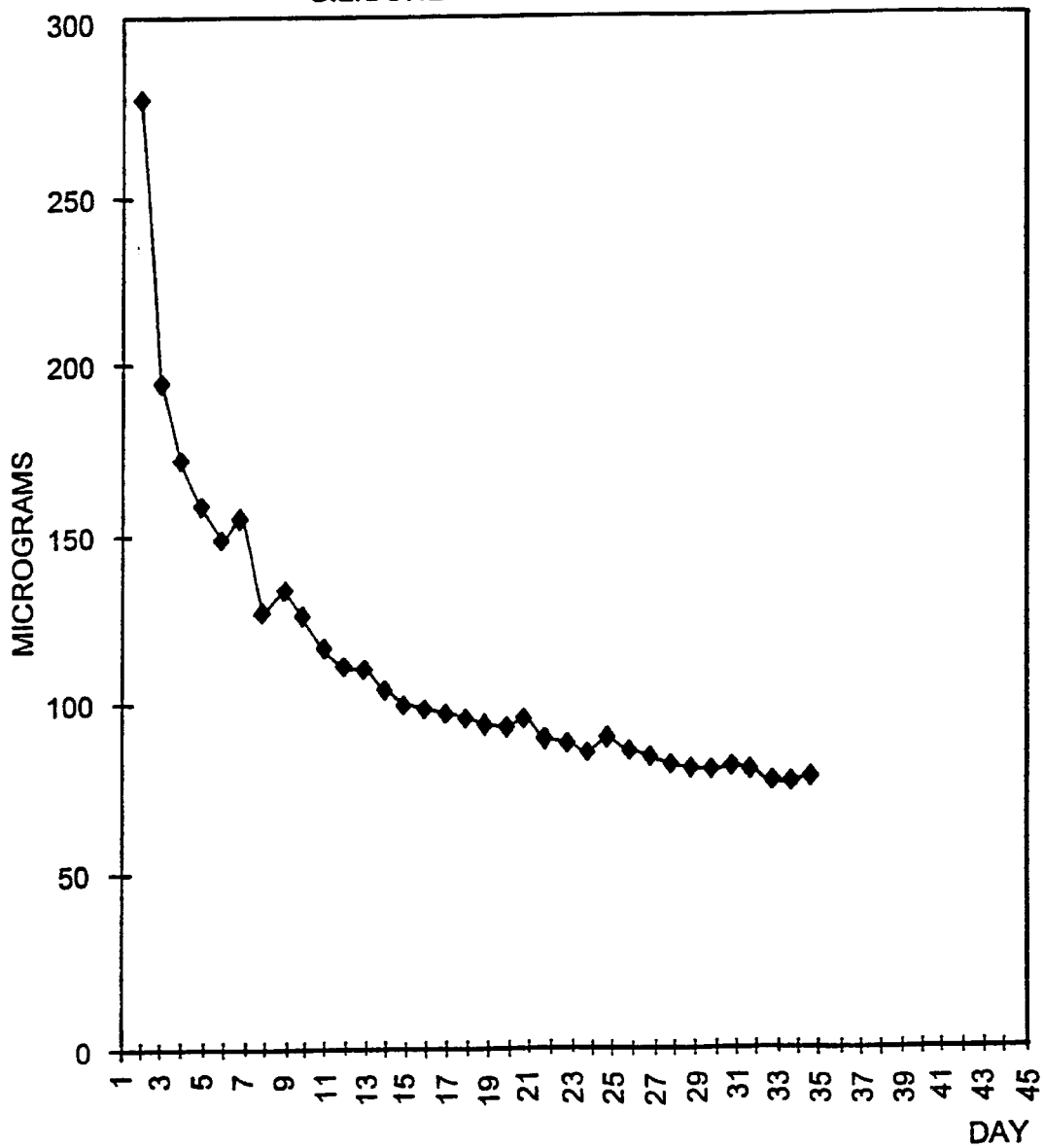

INTRAVAGINAL DRUG DELIVERY DEVICES FOR THE ADMINISTRATION OF TESTOSTERONE AND TESTOSTERONE PRECURSORS

This application is a 371 of PCT/IE98/00033 filed May 7, 1998.

This invention relates to intravaginal drug delivery devices for the administration of testosterone and testosterone precursors to the human or animal female. The term 'precursor' is intended to embrace those compounds which can be readily converted in vivo into testosterone, in which the products of such conversion are clinically and toxicologically acceptable and which compounds possess certain physicochemical properties as defined hereinbelow. In particular, it relates to intravaginal drug delivery devices for the administration of testosterone or a testosterone precursor at a substantially zero order rate over a prolonged period to alleviate or prevent the symptoms associated with testosterone deficiency or, alternatively, to induce supratherapeutic levels.

The intravaginal drug delivery devices of the invention are particularly suitable for the alleviation or prevention of symptoms associated with testosterone deficiency either as a discrete treatment regimen or as an element of hormone replacement therapy in association with oestrogen or combined oestrogen/progestogen drug delivery devices. The clinical efficacy of testosterone replacement therapy, in association with exogenous oestrogen, has been reported from 1950 onwards [2]. The invention may, however, also have application to improve muscle mass and/or bone mass in patients with, for example, AIDS wasting syndrome or osteoporosis, respectively. In addition, the invention may have application as an antiproliferative agent for use against, for example, breast cancer, endometrial cancer, or endometriosis or, alternatively, to treat urogenital or vulval problems.

Plasma concentrations of testosterone in the normal, pre-menopausal, healthy human female are between 0.5 and 2.3 nM (0.15 to 0.65 ng per ml) with a mid-cycle peak [1]. Testosterone deficiency in the premenopausal human female may occur due to disease, oophorectomy, adrenalectomy or traumatic injury. In the postmenopausal female, testosterone deficiency arises primarily from a reduced adrenal output of androstenedione, which is peripherally converted to testosterone in vivo [1].

Testosterone may be administered by intramuscular injection as an oily solution or an aqueous suspension but, when administered by this route, testosterone is rapidly absorbed, metabolised and excreted. Testosterone esters are more hydrophobic than the free steroid and, consequently, are absorbed more slowly than testosterone from the intramuscular route. However, no rate-controlling mechanism is provided and intramuscular injection of a testosterone ester cannot, therefore, provide a substantially zero order pattern of release.

Following oral administration, testosterone or testosterone derivatives are readily absorbed but have poor efficacy because of considerable first-pass hepatic metabolism. Prolonged delivery for at least three weeks in a substantially zero order pattern of release cannot be achieved by the oral route.

GB-B-2 185 187 and GB-B-2 161 073 teach that testosterone may be absorbed across human scrotal skin from a flexible patch over, preferably, 24 hours. A matrix (or non-rate controlled) system for transdermal testosterone delivery to the human female is also known [3]. This system delivers about 1000 μg of testosterone per day, yielding mean circulating plasma testosterone levels of 4–6 nM. Transdermal administration avoids first-pass hepatic metabolism. However, the physical size of transdermal drug delivery systems is such that a new device must be used every few days. This can lead co fluctuations in circulating serum testosterone levels. Furthermore, frequent device replacement is inconvenient and has possible compliance problems for the patient. Although transdermal delivery systems that can maintain substantially constant delivery are known, it is not possible to maintain a substantially zero order delivery for at least three weeks by this route.

Subcutaneous implantation (50 or 100 mg) of testosterone-loaded pellets provides therapy extending to several months and is therefore advantageous in respect of both patient compliance and convenience. However, subcutaneous implants have a number of disadvantages. Specifically, a surgical procedure is required for both insertion and removal of the pellets. In addition, infection, pain and swelling can arise at the insertion site. Furthermore, due to physical size limitations of such systems, it is not possible to make testosterone implants that can deliver the hormone in a substantially zero order pattern over a prolonged period of at least three weeks.

It might be expected that many of the problems associated with long-term testosterone delivery in the human or animal female could be overcome by intravaginal administration of testosterone or testosterone precursors. The vaginal route avoids undesirable first-pass hepatic metabolism. Delivery of testosterone or a testosterone precursor by this route would be expected to be analogous to the natural secretion of testosterone per se into systemic circulation. To achieve substantially zero order pattern of testosterone release, sustained over a period of at least three weeks in order to enhance both patient compliance and convenience, an intravaginal drug delivery device might be expected to be the most suitable drug delivery device. However, there is no teaching of such a device to deliver testosterone at all.

Three basic designs of intravaginal ring are possible, though additional design variations do exist:

(a) The homogeneous or matrix ring, in which the drug is distributed in a polymer matrix. This design is associated with an initial high release of drug, producing a non-physiological circulating plasma level, followed by a decline in the drug release rate as the outer portions of the ring are depleted of drug. Consequently, this ring design cannot deliver the desired substantially constant (or zero order) drug release over a sustained period.

(b) The shell design, in which the drug is contained in a hollow annulus between a drug-free central member and a drug-free sheath or rate-controlling membrane. With this design, burst effects are reduced compared to the homogeneous ring. However, the drug reservoir is physically limited in size and the relative diameters of drug-free central member, hollow drug-containing annulus (polymer matrix) and rate-controlling sheath are such that, where comparatively high daily drug release rates are required, as in supratherapeutic testosterone therapy (e.g. testosterone replacement), this design cannot sustain drug delivery for the desired period of at least three weeks. This design can, of course, sustain drug delivery over at least three weeks, when lower daily drug release rates are required for other indications.

(c) The core design, in which the drug is contained in a core, surrounded by a rate-controlling, drug-free sheath. In this design, high drug loadings are possible and the relative diameters of core and sheath are such that a higher drug release rate can be achieved compared to the shell design. Burst release of drug is reduced compared to the homogeneous ring. Substantially zero order release can be achieved and such release can be sustained for at least three weeks and up to several months due to the higher drug loading possible with this design.

Although intravaginal drug delivery devices containing oestrogens and/or progestogens are long known in the art, there is no teaching in the literature of an intravaginal drug delivery device containing testosterone for any purpose. This is despite intravaginal drug delivery devices being well-known to those skilled in the art and the clinical benefits of testosterone administration being known for many years.

Prejudice against the incorporation of testosterone or a testosterone precursor in an intravaginal drug delivery device in the human or animal female may be at least partially explained by:

(a) The comparatively low apparent permeability coefficient of testosterone across vaginal epithelium, normalised with respect to that of methanol [4]. The apparent permeability coefficient is, in effect, a measure of the ability of a drug to be absorbed from the hydrodynamic layer in the vaginal lumen across the vaginal epithelium into the serosal compartment. The low apparent permeability coefficient of testosterone (0.29) compared to that of, for example, progesterone (0.93) and oestrone (1.00), teaches that a relatively high concentration gradient will be required across the vaginal barrier membrane in order to deliver testosterone into systemic circulation at clinically useful levels [4];

(b) The relatively low aqueous solubility of testosterone itself—25 $\mu$g/ml [4], and the even lower aqueous solubility of the more lipophilic testosterone ester precursors—it would be considered, therefore, to be unlikely that a high enough concentration gradient could be achieved, to deliver clinically useful levels of testosterone into systemic circulation; and (c) A lack of knowledge regarding the daily dosage of testosterone to be delivered in a substantially zero order manner over a prolonged period of at least three weeks such that the circulating systemic levels of testosterone are within the desired range.

Accordingly, it is a novel aspect of the present invention to provide an intravaginal shell or core drug delivery device comprising testosterone or a testosterone precursor as defined hereinbelow in a polymer matrix, surrounded by a sheath. The sheath may be formed from the same material as the polymer matrix, or from other suitable, compatible material known in the art. Said device is capable of releasing testosterone or testosterone precursor in a substantially zero order pattern on a daily basis for a period of at least three weeks.

Said testosterone precursors for human use must possess physicochemical properties such that they can be delivered from an intravaginal drug delivery device at a daily rate that will restore circulating testosterone levels to within the normal physiological range found in the healthy, human, pre-menopausal female (therapeutic levels) or, alternatively, induce supratherapeutic levels. By way of example only, the term "testosterone precursors" includes testosterone esters such as 17 β-alkanoyl esters of testosterone, preferably $C_{1-15}$ saturated or unsaturated straight or branched chain alkanoyl esters, more preferably, testosterone-17-acetate and testosterone-17-propionate.

Whilst the intravaginal device can have any shape and be of any dimensions compatible both with intravaginal administration to the human or animal female and with the requirements imposed by drug delivery kinetics, a particularly preferred device according to the present invention is an elastomeric intravaginal ring. A bullet-shaped pessary is also preferred.

Preferably, daily in vitro release rates of at least 100 $\mu$g testosterone, or of a testosterone precursor equivalent to at least 100 $\mu$g testosterone per se (testosterone equivalent), can be sustained for up to 12 months in a substantially zero order pattern, said daily release rates resulting in the desired therapeutic or supratherapeutic circulating levels of testosterone.

More preferably, the intravaginal drug delivery device is capable of delivering testosterone in a substantially zero order pattern for a period of at least three weeks and up to 12 months at an in vitro daily release rate of at least 100 $\mu$g.

Advantageously, the intravaginal drug delivery device may contain other compatible pharmaceutically active agents. Such pharmaceutically active agents include, but are not limited to, natural or synthetic steroids, for example, oestrogens, progesterones and adrenocortical hormones.

According to a second aspect of the invention there is provided a method of manufacturing an intravaginal shell or core drug delivery device having an outer sheath and a polymer matrix containing testosterone or a testosterone precursor as defined hereinbefore for testosterone administration to the human or animal female. Said method comprises the steps of combining testosterone or a testosterone Precursor and a polymer to form the polymer matrix; and surrounding the polymer matrix with a sheath, whereby the relative amounts of the respective polymer matrix and sheath are chosen, and the geometry of the drug delivery device components selected, to provide a daily substantially zero order pattern release of at least 100 $\mu$g of either testosterone per se or testosterone equivalent for at least three weeks.

The intravaginal drug delivery device may be constructed from one or more biocompatible elastomers compatible with testosterone or the testosterone precursor. Where the elastomer is chosen from the room-temperature vulcanising type of hydroxyl-terminated organopolysiloxanes, suitable cross-linking agents and curing catalysts known in the art may be required. Dimethylpolysiloxane compositions may also be used as the elastomeric component of the intravaginal drug delivery device of the invention.

The geometry of the intravaginal drug delivery device may be chosen such that the daily substantially zero order pattern release of testosterone or a testosterone precursor can be varied up to at least 5000 $\mu$g of testosterone or testosterone equivalent, preferably in the range from 100 to 1500 $\mu$g of testosterone or testosterone equivalent. The term "geometry" encompasses the overall dimensions of the device, as well as, the relative dimensions of the drug/polymer matrix and the sheath. When the device is a ring, the term "geometry" encompasses the overall diameter of the ring; the cross-sectional diameter of the ring; the ratio of the polymer matrix (core or annulus) diameter to the diameter of the whole device in cross-section; and the length of the polymer matrix (core or annulus).

The percentage loading of testosterone or testosterone precursor contained in the polymer matrix can vary from between 1 to 90% w/w. The only importance of the drug loading in a shell or core device design is to ensure that there is sufficient drug present at all times to allow a substantially zero order pattern of drug release to be maintained throughout the required period of sustained drug release. Thus, to ensure maintenance of the substantially zero order drug release pattern throughout the lifetime of the device, the necessary drug loading must be sufficiently in excess of the total drug required to be delivered over the defined sustained-release period.

The intravaginal drug delivery device according to the present invention, as will be exemplified hereinafter, achieves a sufficiently high aqueous concentration of testosterone or testosterone precursor to be expected to promote absorption of testosterone or testosterone precursor through the vaginal epithelial membrane by passive diffusion along a concentration gradient, despite the already mentioned low aqueous solubility of said compounds and despite the already mentioned low apparent permeability coefficient for testosterone.

Several embodiments of the invention will now be described by reference to the General Method of Manufacture of an intravaginal drug delivery device according to the invention and will be exemplified by reference to the following Examples. It should be understood that these examples are disclosed solely by way of further illustrating the invention and should not be taken in any way to limit the scope of said invention. Thus, for instance, it will be obvious to those skilled in the art that the technique of injection moulding referred to therein may be replaced in whole or in part by other manufacturing techniques that will produce the same end product, for example, the technique of extrusion.

General Method of Manufacture

An elastomer mix is prepared by blending 97 parts by weight of a hydrophobic elastomeric polymer containing about 25% w/w diatomaceous earth as the filler with 2.5 parts by weight of a cross-linking agent, n-propylorthosilicate. A suitable hydrophobic elastomeric polymer is stannous octoate-cured polydimethylsiloxane polymer, two suitable examples of which are those known as Dow Corning QCF7 3099 and Nusil Med 7.6382.

An active mix is formed by blending 85 parts by weight of the elastomer mix, 5 parts by weight of barium sulphate and 10 parts by weight of testosterone or testosterone precursor.

The core of a core intravaginal drug delivery device of the invention is produced by mixing 200 parts by weight of the active mix with 1 part by weight of an activating catalyst, stannous octoate. The resultant core mix is injected into a core mould and cured at 80° C. for 2 minutes. The mould is then opened and the core is removed and trimmed.

The sheath mix is formed by mixing 200 parts by weight of the elastomer mix with 1 part by weight of an activating catalyst, for example, stannous octoate. An intravaginal drug delivery device in the form of a half ring is produced by injecting the sheath mix into a half ring mould containing a previously prepared core and then curing at 80° C. for 2 minutes. The mould is then opened, following which the half ring is removed and trimmed.

An intravaginal drug delivery device in the form of a complete ring is produced by injecting the sheath mix into a full ring mould containing the previously prepared half ring and then curing at 80° C. for 2 minutes. The mould is then opened, following which the full ring is removed and trimmed.

With a drug loading of 10% or less, it is possible to hand inject the core mix into the mould. However, as the drug loading is increased, the viscosity of the core mix increases and it becomes necessary to extrude the core mix into the mould.

The geometric characteristics of the ring can be varied as required by the use of appropriately sized moulds or extrusion nozzles, as will be obvious to those skilled in the art.

It will be appreciated that a shell intravaginal drug delivery device would be analogously prepared, although not specifically described herein.

EXAMPLE 1

Intravaginal testosterone-containing drug delivery devices in the form of rings were prepared by following the General Method of Manufacture set out hereinabove, with a ring geometry of: 9 mm (cross-sectional diameter), 54 mm (outer diameter), 4.8 mm (core diameter) and with core lengths of 30, 60 and 90 mm, respectively.

EXAMPLE 2

Intravaginal testosterone-17-acetate-containing drug delivery devices in the form of rings were prepared by following the General Method of Manufacture set out hereinabove, with a ring geometry of: 9 mm (cross-sectional diameter), 54 mm (outer diameter), 4.8 mm (core diameter) and with core lengths of 30, 60 and 90 mm, respectively.

The in vitro release characteristics of the intravaginal rings of Examples 1 and 2 are illustrated by reference to Tables 1–4. Four identical rings were prepared for each compound according to the General Method of Manufacture, the elastomer mix being a stannous octoate-cured polydimethylsiloxane polymer. The rings were tested in vitro at a constant temperature of 37° C. for their release characteristics in a sufficient volume (250 ml) of each of the following media: 0.9% (w/v) saline and 1.0% (w/v) aqueous benzalkonium chloride (BKC). The saline medium was chosen because the ability of testosterone or a particular testosterone precursor to achieve substantial release from an intravaginal ring into saline may be an indicator of its likely in vivo absorption characteristics. The benzalkonium chloride-containing medium was chosen to ensure 'sink conditions' in at least one medium for each intravaginal ring—'sink conditions' refers to that set of in vitro conditions which effectively simulates the active haemoperfusion that occurs in vivo, and which results in a maximum drug diffusion rate, at any given time, across the aqueous boundary layer.

Thus, each ring was suspended by a thread in an individual enclosed flask containing the dissolution medium, maintained at a constant temperature of 37° C. The contents of the flask were gently agitated in order to prevent the occurrence of a hydrostatic layer on the surface of the ring. After 24 hours (±30 minutes), the ring was removed and suspended in a flask of fresh dissolution medium of identical volume. This process was repeated daily until 17 days had elapsed. At the end of each 24 hour period, a sample of the dissolution medium was analysed, for its testosterone and, if appropriate, testosterone precursor content by HPLC, using reverse phase packing and UV detection at 240 nm for testosterone or testosterone-17-acetate, with reference to the appropriate standard solutions. Due to minor hydrolysis to testosterone during storage, testosterone-17-acetate concentrations were determined by analysis for both testosterone and testosterone-17-acetate.

The analytical method for testosterone has a precision of less than 2% RSD (relative standard deviation) and the analytical method for testosterone-17-acetate has an RSD of less than 4%. The sensitivity of the testosterone analytical method is 5 µg per ml.

TABLE 1

In vitro release into 0.9% saline (as total testosterone)
Core Loading: 10% w/w testosterone

| Core length (mm) | DAY (μg/day) | | | | | | | | | |
|---|---|---|---|---|---|---|---|---|---|---|
| | 2 | 3 | 5 | 8 | 9 | 10 | 13 | 15 | 16 | 17 |
| 30 | 270 | 232 | 237 | 228 | 229 | 226 | 238 | 227 | 216 | 224 |
| 60 | 471 | 401 | 419 | 400 | 407 | 406 | 430 | 408 | 392 | 388 |
| 90 | 696 | 572 | 588 | 592 | 589 | 581 | 623 | 595 | 584 | 612 |

TABLE 2

In vitro release into 1.0% BKC (as total testosterone)
Core Loading: 10% w/w testosterone

| Core length (mm) | DAY (μg/day) | | | | | | | | | |
|---|---|---|---|---|---|---|---|---|---|---|
| | 2 | 3 | 5 | 8 | 9 | 10 | 13 | 15 | 16 | 17 |
| 30 | 271 | 222 | 236 | 233 | 234 | 240 | 249 | 244 | 243 | 250 |
| 60 | 512 | 433 | 459 | 455 | 461 | 484 | 476 | 468 | 476 | 477 |
| 90 | 744 | 633 | 671 | 661 | 674 | 719 | 706 | 692 | 713 | 709 |

TABLE 3

In vitro release into 0.9% saline (as total testosterone)
Core Loading: 10% w/w testosterone-17-acetate

| Core length (mm) | DAY (μg/day) | | | | | | | | | |
|---|---|---|---|---|---|---|---|---|---|---|
| | 2 | 3 | 5 | 8 | 9 | 10 | 13 | 15 | 16 | 17 |
| 30 | 247 | 260 | 316 | 325 | 310 | 306 | 302 | 318 | 311 | 297 |
| 60 | 320 | 350 | 571 | 596 | 603 | 587 | 596 | 578 | 599 | 605 |
| 90 | 568 | 556 | 700 | 759 | 723 | 718 | 768 | 751 | 750 | 771 |

TABLE 4

In vitro release into 1.0% BKC (as total testosterone)
Core Loading: 10% w/w testosterone-17-acetate

| Core length (mm) | DAY (μg/day) | | | | | | | | | |
|---|---|---|---|---|---|---|---|---|---|---|
| | 2 | 3 | 5 | 8 | 9 | 10 | 13 | 15 | 16 | 17 |
| 30 | 1944 | 1576 | 1542 | 1556 | 1541 | 1557 | 1562 | 1549 | 1540 | 1558 |
| 60 | 3430 | 3216 | 3004 | 3089 | 3010 | 2996 | 3101 | 3056 | 3025 | 3076 |
| 90 | 5997 | 5148 | 4238 | 4488 | 4302 | 4601 | 4459 | 4523 | 4493 | 4528 |

Tables 1 and 2 show the daily in vitro release rates of testosterone into saline and BKC over a continuous period of 17 days. 'Sink conditions' were evident for testosterone in 0.9% saline.

Tables 3 and 4 show the daily in vitro release rates of the testosterone precursor, testosterone-17-acetate, into saline and BKC. As expected from the more lipophilic nature of testosterone-17-acetate, the in vitro release rates into BKC are considerably higher than those into saline, indicating that 'non-sink conditions' exist in saline and that 'sink conditions', only arise when a solubilising medium such as BKC is employed.

The in vitro release data into saline (Tables 1 and 3) confirm that vaginal fluid bioavailability would be expected for each of testosterone and testosterone-17-acetate. Thus, a suitable concentration gradient would, surprisingly, be expected to exist across the vaginal epithelium, for each of testosterone and testosterone-17-acetate, despite the relatively low aqueous solubility for testosterone and the even lower expected aqueous solubility of the more lipophilic testosterone precursors.

The in vitro release data into BKC (Tables 2 and 4) confirm that absorption across the vaginal barrier membrane would be expected to occur and that, therefore, systemic bioavailability, for each of testosterone and testosterone-17-acetate, would, surprisingly, the expected, despite the low apparent permeability coefficient for testosterone.

EXAMPLE 3

Intravaginal testosterone-containing drug delivery devices in the form of rings were prepared by following the General Method of Manufacture set out hereinabove, with a ring geometry of 7.6 mm (cross-sectional diameter), 56 mm (outer diameter), 4.5 mm (core diameter) and with core lengths of 65 mm, 110 mm and 130 mm, respectively.

The in vitro release characteristics of the intravaginal rings of this Example are illustrated by reference to Table 5. Duplicate rings were tested in vitro at a constant temperature of 37° C. for their release characteristics in a sufficient volume (500 ml–1 l) of 0.9% (w/v) saline using the method described in Example 2, except that the time period was extended to a 30 day period.

TABLE 5

In Vitro Release of Testosterone (μg/day)

| Day | Core Length | | |
|---|---|---|---|
|  | 65 (mm) | 110 (mm) | 130 (mm) |
| 1 | 589 | 973 | 1185 |
| 2 | 498 | 875 | 1043 |
| 3 | 513 | 858 | 1082 |
| 4 | 532 | 896 | 1044 |
| 5 | 508 | 854 | 973 |
| 6 | 486 | 851 | 1051 |
| 7 | 523 | 931 | 1016 |
| 8 | 525 | 863 | 1050 |
| 9 | 520 | 820 | 1017 |
| 10 | 524 | 859 | 1019 |
| 11 | 526 | 850 | 992 |
| 12 | 504 | 886 | 1014 |
| 13 | 522 | 846 | 1009 |
| 14 | 512 | 797 | 1009 |
| 15 | 508 | ND* | 1007 |
| 16 | 510 | ND | ND |
| 21 | 496 | 792 | 981 |
| 22 | 483 | 769 | 943 |
| 23 | 486 | 788 | 944 |
| 28 | 472 | 745 | 901 |
| 29 | 458 | ND | 898 |
| 30 | 469 | ND | 891 |

*ND: Not Determined

It will be observed that testosterone is released in a substantially zero order pattern, over the 30 day monitoring period.

EXAMPLE 4

Intravaginal testosterone-containing drug delivery devices in the form of rings were then evaluated for their in vivo release characteristics. Specifically, rings of Example 3 having core lengths of 65 mm and 110 mm were each tested in four women, all of whom had normal baseline testosterone levels and were at least one year post-menopause. Testosterone levels were measured at regular intervals and the resulting release characteristics over time are illustrated in FIG. 1. After an initial lag phase, substantially zero order release was observed in vivo from day 5 (the first post day 1 measurement) to day 28 (the last day of measurement).

EXAMPLE 5

Intravaginal testosterone-17-propionate-containing drug delivery devices in the form of rings were prepared by following the General Method of Manufacture set out hereinabove, with a ring geometry of 7.6 mm (cross-sectional diameter), 56 mm (outer diameter), 2 mm (core diameter) and a core length of 90 mm.

The in vitro release characteristics of this ring are illustrated with reference to Table 6. Duplicate rings were tested in vitro at a constant temperature of 37° C. for their release characteristics in a sufficient volume (1 l) of 0.9% (w/v) saline, using the method described in Example 2, except that the time period was 26 days, the sample being analysed at 240 nm for testosterone-17-proprionate.

TABLE 6

In Vitro Release of Testosterone-17-propionate

| Day | Release Rate (μg/day) |
|---|---|
| 2 | 171 |
| 3 | 328 |
| 4 | 337 |
| 5 | 465 |
| 7 | 457 |
| 13 | 527 |
| 14 | 587 |
| 19 | 585 |
| 20 | 663 |
| 26 | 637 |

It will be observed that, following a lag phase of 13 days testosterone-17-propionate is released in a substantially zero order pattern over a 13 day monitoring It is believed that the initial lag phase, rather than the burst phase usually observed, results from the fact that the rings were freshly made and not stored for a desired period of at least one month before use.

If freshly made rings are to be used, it is suggested that such rings be soaked for at least 5 days in 0.9% (w/v) saline or tap water before use. This measure will reduce or eliminate the lag phase, if such is desired. Alternatively, such a lag phase may be desired, to allow the patient to gradually acclimatise to the rising testosterone levels and, in that event, freshly made, unpre-soaked rings should be used.

In a routine commercial setting, it is recommended that rings stored at room temperature would have a 3 year shelf life. Thus, the lag phase observed with these freshly made rings is unlikely to arise unless rings are specifically made for immediate use for certain clinical indications.

On the other hand, if rings are to be stored for a prolonged storage period, a burst phase is initially observed. Such a burst phase can be reduced or eliminated, if the ring is pre-soaked for 24 hours in 0.9% (w/v) saline or tap water.

For high dose applications, testosterone-17-propionate is preferred over testosterone because the amounts released are greater, thereby permitting shorter core lengths and opening up the possibility of co-administration, in a substantially zero order pattern, of other pharmaceutically active agents.

EXAMPLE 6

Intravaginal testosterone-containing drug delivery devices in the form of pessary bullets as shown in FIG. 2 were prepared as follows:

0.50 g of testosterone was dispersed in 4.50 g of the elastomer mix (100 parts of tetrapropoxysilane-crosslinked silicone (MED-6382, Nusil) as the elastomer base and 2.5 parts tetrapropoxysilane (NPOS). 0.025 g of stannous octoate catalyst (0.5% of active mix) was added, thoroughly mixed and injected into a 22.4 mm by 10.0 mm pessary mould (inner small bullet (discontinuous outline) of FIG. 2). The mixture was cured at 60° C. for 5 minutes, to produce pessaries weighing 1.1±0.1 g, equivalent to 110 mg of testosterone per pessary.

Approximately four grams of the inactive elastomer mix, including 2.5% catalyst, were injected into a 37.2 mm by 21.6 mm pessary mould (larger bullet of FIG. 2). The testosterone-containing pessary was then set into the inactive elastomer mix within the larger pessary mould. The mould was then filled with excess inactive elastomer mix and cured at 60° C. for 5 minutes, to produce full reservoir pessaries weighing 9.0±0.3 g.

The in vitro release characteristics are illustrated in FIG. 3. Duplicate bullets were tested in vitro at a constant temperature of 37° C. for their release characteristics in a sufficient volume (1l) of 0.9% (w/v) saline, using the method described in Example 2. Following an initial burst phase, substantially zero order release of testosterone was observed over a prolonged period of time.

It is thought that the initial burst phase might be reduced or eliminated, if this is desired, by pre-soaking the bullet in 0.9% (w/v) saline or tap water for several days.

REFERENCES CITED

1. Wilson, J. D. (1996) Androgens. In: *Goddman and Gilman's The Pharmacological Basis Of Therapeutics*, Ninth Edition (Hardman, J. G. and Limbird, L. E., eds.). McGraw-Hill, New York. pp. 1441–1457.

2. Greenblatt, R. B. et al. (1950) *Journal of Clinical Endocrinology and Metabolism* vol. 10:15 pp. 47–52.

3. Buckler, H. M. et al (1997). Pharmacokinetics of a novel transdermal delivery system for testosterone in women. Abstract. 14th Joint meeting of British Endocrine Societies.

4. Chien, Y. W. (1982) *Novel Drug Delivery Systems* Marcel Dekker, New York, pp. 69–71.

What is claimed is:

1. An intravaginal core drug delivery device suitable for administration to a female, the device comprising testosterone or a testosterone precursor in a polymer matrix and surrounded by a sheath, the device being capable of releasing the testosterone or testosterone precursor in a substantially zero order pattern on a daily basis for at least three weeks, the testosterone or testosterone precursor possessing physiochemical properties such that they may be delivered from the device at a daily rate that will restore circulating testosterone levels to the normal physiological range or, alternatively induce supra therapeutic testosterone levels and the testosterone precursor being metabolisable, in viva, to release testosterone.

2. The intravaginal device according to claim 1, in which the testosterone precursor is an ester.

3. The intravaginal device according to claim 2, in which the ester is a 17 β-alkanoyl ester.

4. The intravaginal device according to claim 1, in which the testosterone precursor is selected from testosterone-17-acetate and testosterone-17-propionate.

5. The intravaginal device according to claim 1, in which the device is capable of releasing at least 100 μg testosterone per day or testosterone precursor equivalent to at least 100 μg testosterone per day for at least three weeks.

6. A method of restoring circulating testosterone levels in a subject to within the normal physiological range, comprising applying to the subject the device of claim 1 so as to restore circulating testosterone levels in the subject to within the normal physiological range.

7. A method of inducing supra therapeutic testosterone levels in a subject, comprising applying into the vagina of the subject the device of claim 1 so as to induce supra therapeutic testosterone levels in the subject.

8. The intravaginal device according to claim 1, in which the device is capable of releasing at least 100 μg of testosterone per day or testosterone precursor equivalent to at least 100 μg testosterone per day for up to twelve months.

9. A method of manufacturing an intravaginal core drug delivery device having an outer sheath and a polymer matrix containing testosterone or a testosterone precursor, the method comprising the steps of combining testosterone or a testosterone precursor and a polymer to form the polymer matrix; and surrounding the polymer matrix with the sheath, whereby the relative amounts of the respective polymer matrix and sheath are selected, and the geometry of the drug delivery device components is selected, to provide for at least three weeks a daily substantially zero order pattern release of at least 100 μg of testosterone or testosterone precursor equivalent to at least 100 μg of testosterone.

\* \* \* \* \*